US 8,043,811 B2

(12) United States Patent
Danks et al.

(10) Patent No.: US 8,043,811 B2
(45) Date of Patent: Oct. 25, 2011

(54) PURIFICATION METHOD AND KITS

(75) Inventors: Christopher Danks, York (GB); Neil Boonham, York (GB)

(73) Assignee: The Food & Environment Research Agency (FERA) representing the Secretary of State for Environment, Food and Rural Affairs, York (GB)

(*) Notice: Subject to any disclaimer, the term of this patent is extended or adjusted under 35 U.S.C. 154(b) by 0 days.

(21) Appl. No.: 12/282,247

(22) PCT Filed: Mar. 12, 2007

(86) PCT No.: PCT/GB2007/000865
§ 371 (c)(1), (2), (4) Date: Oct. 2, 2008

(87) PCT Pub. No.: WO2007/104962
PCT Pub. Date: Sep. 20, 2007

(65) Prior Publication Data
US 2009/0098560 A1    Apr. 16, 2009

(30) Foreign Application Priority Data

Mar. 11, 2006   (GB) .................................. 0604973.8

(51) Int. Cl.
C12Q 1/68      (2006.01)
C12P 19/34     (2006.01)
C07H 21/00     (2006.01)
G01N 33/53     (2006.01)
C07H 21/02     (2006.01)
C07H 21/04     (2006.01)

(52) U.S. Cl. ........ 435/6.1; 435/91.2; 435/7.1; 536/23.1; 536/25.4

(58) Field of Classification Search .................. None
See application file for complete search history.

(56) References Cited

U.S. PATENT DOCUMENTS

| 5,955,351 | A | 9/1999 | Gerdes et al. |
| 6,103,192 | A | 8/2000 | Stapleton et al. |
| 6,140,134 | A | 10/2000 | Rittenburg |
| 2002/0001852 | A1 | 1/2002 | Mendel-Hartvig et al. |
| 2002/0110803 | A1 | 8/2002 | Dhar et al. |
| 2002/0150907 | A1 | 10/2002 | Fomovskaia et al. |
| 2004/0096958 | A1 | 5/2004 | Pottathil et al. |
| 2006/0019406 | A1 | 1/2006 | Wei et al. |

FOREIGN PATENT DOCUMENTS

| WO | 97/09620 | 3/1997 |
| WO | 99/46591 | 9/1999 |
| WO | 00/29112 | 5/2000 |

(Continued)

OTHER PUBLICATIONS

Lockley, A. K. et al., Nucl. Acids Res., vol. 25, pp. 1313-1314 (1997).*

(Continued)

Primary Examiner — Teresa E Strzelecka
(74) Attorney, Agent, or Firm — Nixon & Vanderhye P.C.

(57) ABSTRACT

A method for separating nucleic acid from a liquid sample, said method comprising the steps of causing a liquid sample containing or suspected of containing said nucleic acid to flow along a bibulous membrane, for example of a conventional lateral flow device, so that nucleic acid is distributed along the length of the membrane. The nucleic acid may be detected on the membrane.

42 Claims, 5 Drawing Sheets

FOREIGN PATENT DOCUMENTS

| WO | WO 00/31538 | 6/2000 |
|---|---|---|
| WO | 00/78917 | 12/2000 |
| WO | 01/11355 A1 | 2/2001 |
| WO | 01/66688 A1 | 9/2001 |
| WO | WO 01/66688 | 9/2001 |
| WO | 2004/065010 | 8/2004 |
| WO | 2004/099383 | 11/2004 |
| WO | 2006/003394 | 1/2006 |

OTHER PUBLICATIONS

Tribodet, M. et al., J. Gen. Virol., vol. 86, pp. 2101-2105 (2005).*

Danks, C. et al., EPPO Bulletin, vol. 30, pp. 421-426 (2000).*

International Search Report for PCT/GB2007/000865, mailed Jul. 11, 2007.

Written Opinion of the International Searching Authority for PCT/GB2007/000865, mailed Jul. 11, 2007.

Great Britain Search Report for GB Application No. 0604973.8, dated Jul. 10, 2006.

Tomlinson, J. A. et al., "On-site DNA extraction and real-time PCR for detection of Phytophthora ramorum in the field", Applied and Environmental Microbiology, vol. 71, No. 11, pp. 6702-6710, (Nov. 2005).

Singh, R. P. et al., "Evaluation of a simple membrane-based nucleic acid preparation protocol for RT-PCR detection of potato viruses from *aphid* and plant tissues", Journal of Virological Methods, vol. 121, No. 2, pp. 163-170, (Nov. 2004).

Ward, E. et al., "Plant pathogen diagnostics: immunological and nucleic acid-based approaches", Annals of Applied Biology, vol. 145, No. 1, pp. 1-16, (2004).

O'Keeffe, M. et al., "Preliminary evaluation of a lateral flow immunoassay device for screening urine samples for the presence of sulphamethazine", Journal of Immunological Methods, vol. 278, No. 1-2, pp. 117-126, (Jul. 2003).

Fong, W. K. et al., "Rapid solid-phase immunoassay for detection of methicillin-resistant *Staphylococcus aureus* using cycling probe technology", Journal of Clinical Microbiology, vol. 38, No. 7, pp. 2525-2529, (Jul. 2000).

Cambell, K. et al., "Development and validation of a lateral flow device for the detection of nicarbazin contamination in poultry feeds", Journal of Agricultural and Food Chemistry, vol. 55, No. 6, pp. 2497-2503, (Mar. 2007).

Liu, J. et al., "A simple and sensitive "dipstick" test in serum based on lateral flow separation of aptamer-linked nanostructures", Angewandte Chemie, vol. 45, No. 47, pp. 7955-7959, (Dec. 4, 2006).

Lane, C. R. et al., "Diagnosis of *Phytophthora ramorum*—evaluation of testing methods", bulletin OEPP, vol. 36, No. 2, pp. 389-392, (Aug. 2006).

Courtjens, P. et al., "Use of Up-Converting Phosphor Reporters in Lateral-Flow Assays to Detect Specific Nucleic Acid Sequences: A Rapid, Sensitive DNA Test to Identify Human Papillomavirus Type 16 Infection", Clinical Chemistry, vol. 47, No. 10, pp. 1885-1893, (2001).

Dineva, M. A. et al., "Simultaneous Visual Detection of Multiple Viral Amplicons by Dipstick Assay", Journal of Clinical Microbiology, vol. 43, No. 8, pp. 4015-4021, (Aug. 2005).

United Kingdom Examination Report under Section 18(3) dated Jun. 3, 2011, issued in connection with GB 1101598.9.

United Kingdom Examination Report under Section 18(3) dated Jun. 17, 2011, issued in connection with GB1101598.9.

McCabe, "Utility of PCR for DNA Analysis from Dried Blood Spots on Filter Paper Blotters", PCR Methods and Applications 1:99-106, 1991, published by Cold Spring Harbor Laboratory Press.

\* cited by examiner

PURIFICATION METHOD AND KITS

This application is the U.S. national phase of International Application No. PCT/GB2007/000865, filed 12 Mar. 2007, which designated the U.S. and claims priority to Great Britain Application No. 0604973.8, filed 11 Mar. 2006, the entire contents of each of which are hereby incorporated by reference.

The present invention relates to a novel purification method, which may be used in a wide variety of assays, as well as to reagents and kits useful in said method.

A wide variety of assay methods are utilised in diagnostics or detection. The detection of analytes such as proteins on a variety of solid supports is well known in the art. Many such tests are in the form of "dipstick" assays which rely on lateral flow of liquid sample containing the analyte along a membrane, where they encounter labels, labelled binding partners and/or immobilised binding partners, in a sequence whereby a detectable visible signal is developed on the membrane. Such methods are advantageous in that they provide rapid results, and may be used by unskilled operators in almost any location.

For instance, they may be utilised in agriculture to detect particular pests or pathogens on crop plants, such as fungal antigens or viral infections.

In certain situations a simple positive or negative result, indicative of the presence or absence of analyte, is all that is necessary. For example such assays are commonly used in pregnancy tests, and the mere presence of a specific hormone, such as HCG, is indicative that that subject is pregnant.

However, in many instances, test of this type can give only a preliminary diagnosis of a possible problem or condition. In the case of many microorganisms for example, the presence of a particular protein may be indicative of the presence of a particular type of organism, such as the general bacterial, fungal or viral class that is present, but the precise strain of the organism may not be detectable in this way. Since the precise strain is frequently critical in determining the precise level of risk any particular scenario, further investigations are required. For instance, there may be many stains of a particular bacteria such as E. coli or virus such as flu viruses, but only particular strains such as E. coli 0157 or avian flu H5N1 strain which presents a significant health risk. Precise diagnosis of these strains may be difficult since antibodies used in diagnostic techniques may react or cross react with proteins from various strains.

Alternative methods of detection or diagnosis act at the nucleic acid level. In these methods, particular nucleic acid sequences, such as DNA or RNA sequences are detected in samples, and this indicates the presence of particular organisms. These techniques are very sensitive, and by selection of suitable characteristic target nucleic acids, precise strains or even precise allelic or genomic forms of particular genes, which may be characteristic of genomic disease or a predisposition to certain disease states may be detected.

Amplification techniques such as the polymerase chain reaction (PCR) or reverse-transcriptase-polymerase chain reaction (RT-PCR) mean that these techniques can be employed even when the amount of nucleic acid present or likely to be present in an assay is very low indeed.

Thus, these techniques are a powerful tool in the detection and diagnosis area.

However, these techniques in general require some significant sample preparation methods. It is frequently necessary to carry out a significant amount of purification or preparation of samples such as crude extracts from tissues such as plant or animal tissue, or blood or urine samples, in order to remove moieties within the sample, which would inhibit the nucleic acid detection method, or mask the results. As a result, it is frequently difficult to carry out these tests outside of a laboratory environment, and therefore samples taken must be transported for further analysis.

Transport of liquid samples containing genetic material can be difficult, requiring sterility of collection of such samples, and/or freezing of samples. Temporary storage of samples containing genetic material such as blood, dried onto nucleic acids on solid supports, and in particular membranes such as filter papers and the like is known. However, it is generally perceived that there may be problems with stability of such stored material, and methods for improving this, involving impregnation of the solid support with various chemical reagents, including weak bases and chelating agents, has been suggested (see for example U.S. Pat. No. 5,756,126).

Storage cards which purport to carry out certain preliminary sample preparation steps, such as cell lysis and protein denaturation, as well as potentially adding reagents such as PCR primers which may be utilised in subsequent analysis is also disclosed in U.S. Pat. No. 5,756,126, and are available from Whatman as FTA cards. These carry specific reagents such as chelating agents, bases and ionic detergents to facilitate the storage capability.

Attempts have been made to allow for the detection of nucleic acids directly on membranes, using complex devices and systems that utilise binding agents for specific nucleic acids, haptens and/or labelled moieties generate a signal, not unlike that found with a conventional protein analyte (see for example WO 00/29112 and Dinerva et al., J. of Clin. Microbiol. (2005) p 4015-4021). Generally in these instances, it is necessary to amplify for example using a polymerase chain reaction in order to get sufficient of the target DNA present in the sample to provide a detectable signal.

The applicants have found however that a conventional liquid lateral flow device, as used for instance in a dipstick type immunoassay can provide an excellent means of purification and storage of nucleic acids, ready for subsequent analysis.

According to the present invention, there is provided a method for separating nucleic acid from a liquid sample, said method comprising the steps of causing a liquid sample containing or suspected of containing said nucleic acid to flow along a bibulous membrane, so that nucleic acid is distributed along the length of the membrane.

The applicants have found that when allowed to flow along a bibulous membrane, including under the type of conditions used in a liquid flow device, nucleic acids become bound to the membranes, in particular the cellulose or nitrocellulose membranes, used in these devices. It appears that by allowing a liquid sample to pass along a bibulous membrane, any nucleic acids present are retained preferentially on the membrane and so can be separated from other components in the sample. Under these circumstances, they become distributed along the length of the membrane, in particular along substantially all and suitably the entire length of the membrane, in a form in which they are stable. There is no need to provide specific binding agents on the membrane to ensure that the nucleic acids are retained or concentrated in a particular area or to prevent complete elution off the membrane. This makes the device simpler and more economical to produce. The presence of nucleic acids on the membrane can be detected using any of the conventional detection methods.

The presence of nucleic acid on the membrane may subsequently be detected or nucleic acid may subsequently be recovered from said membrane, either before or after the membranes have been allowed to dry.

As a result, these membranes provide readily available, and easy to use purification means, which can be utilised in a wide variety of applications. Fields in which this may be used include food and agriculture testing, diagnostics (including human, veterinary diagnostics), environmental monitoring (including water and soil monitoring), forensics, transgenics, transfusion medicine, plasmid screening, drug discovery, genomics, plant or animal identification or classification, pharmacogenetics, STR analysis and molecular biology research.

For instance, the method of the invention can be carried out as a preliminary step to any form or genetic analysis, such as SNP typing, DNA fingerprinting or nucleic acid sequencing, as well as in detection of specific nucleic acid, which may be useful in the diagnosis of diseases or the detection of pathogens.

Once separated on the membrane, the nucleic acid may be subjected to further analysis in situ, or if necessary, nucleic acid may be eluted from or otherwise removed from the membrane using a suitable buffer, and the analysis carried out on the eluate or extract.

The membrane may be utilised in place of a conventional purification column, and represents a much more economical and easy to use option.

The applicants have found also that the nucleic acids remain in place and stable on membranes, which have been allowed to dry, for extended periods of time, including many years. As a result, samples can be stored or even archived for extended periods prior to analysis.

The membrane is suitably an element of a conventional liquid flow device.

As used herein, the term "liquid flow device" refers to a device comprising a porous or bibulous membrane, through which a liquid sample and reagents including, in some instances, labelled reagents may pass. These may include the well-known lateral flow devices (LFDs).

The nucleic acid, which is recovered or detected may be, for example, a nucleic acid which is characteristic of a particular organism, such as a pathogenic organism for example a virus, fungus or bacteria, or more suitably, a nucleic acid which is characteristic of a particular pathogenic strain or species of such an organism.

Alternatively, for diagnostic purposes, it may comprise a specific nucleic acid sequence which is characteristic of a genetic disease condition in a plant or animal, including humans, or of a predisposition to a genetic disease or condition, in which case, it may be necessary to detect the presence of more or more polymorphisms or variations within the sequence.

As discussed above, isolation of nucleic acids for analytical purposes is widely used in a broad range of fields, and the present invention may be used in any of these.

Multiple nucleic acid sequences may be detected on or recovered from the membrane. These may be from the same or different sources, depending upon the purpose of the test. For instance, if one is seeking to identify the presence of an infective organism within a sample, one might wish to detect not only a nucleic acid, which is characteristic of the organism, but also a nucleic acid, which is characteristic of the host organism in order to confirm the veracity of the sample.

This may be done for example by detecting more than one nucleic acid on a particular sample of the membrane (for example using a multiplex PCR) or by subjecting different samples of the membrane to different detection reactions.

As used herein, the term "membrane" refers to solid matrices which are generally planar in nature and porous. Suitable matrices or membranes may comprise cellulose based materials such as cellulose, nitrocellulose, or carboxymethylcellulose, hydrophilic polymers including synthetic hydrophilic polymers such as polyesters, polyamides, carbohydrate polymers, hydrophobic polymers such as halogenated polymers such as polytetrafluoroethylene, fibreglass or porous ceramics.

Particularly suitable membranes include cellulose membranes and in particular nitrocellulose membranes which may be laminated, such as those available from Millipore. These may be supported on a backing material such as a plastic backed membrane such as a polyester (Mylar®) or PET backed cellulose membrane. The pore size of the membrane may be varied widely. The applicants have found that the pore size does not appear to be critical for the retention or otherwise of the nucleic acids. Membranes which have lateral flow rates across a 4 centimeter length of membrane in the range of from 35-240 seconds are available, suitably from 65-180 seconds, are effective in the method of the invention. This generally correlates to a pore size and/or formulation of the membrane material such as nitrocellulose as would be understood in the art.

The devices may take various forms, but in general, they comprise a sample receiving section, which is either a section of the membrane itself or an absorbent pad, which is in liquid contact with the membrane. Membranes themselves are suitably in the form of an elongate strip, along which liquid deposited in the sample receiving section is able to travel. An absorbent pad may be located at an end of the membrane remote from the sample receiving section in order to absorb excess sample and also to effectively draw the liquid sample along the membrane.

Suitably the membrane at least is accommodated within a solid housing such as a plastics housing, which may be provided with one or more openings or windows for sample delivery and/or for reading results when these are utilised in a conventional immunoassay procedure. Alternatively, the sample receiving section may be provided outside of the housing.

However, unhoused dipstick structures, in particular if laminated for support and protection may be preferred in some instances, in particular for laboratory use.

In one embodiment, the method can be used in an assay for detecting the presence of a specific nucleic acid in a liquid sample.

The sample applied is suitably any liquid sample which contains or is suspected of containing nucleic acid sequences. Thus samples comprise a liquid having dissolved, suspended, mixed or otherwise contained therein, nucleic acid (including DNA and/or RNA), or cells, cell components or cell extracts which contain DNA and/or RNA.

Samples of this nature may be derived from a wide variety of sources. This includes for instance, physiological, pathological or clinical body liquids such as secretions, excretions, exudates and transudates of humans or animals, as well as cell suspensions such as blood, serum, lymph, synovial fluid, semen, saliva (in particular containing buccal cells), skin scrapings and hair root cells taken from animals including humans. Additional samples may include physiological or pathological liquids or cell suspensions of plants, liquid products such as extracts or suspensions of bacteria, fungi, plasmids or viruses etc., and liquid products, extracts or suspensions of pararsites such as helminths, protozoas, spirochetes. Liquid samples obtained by forming tissue extracts for example plant or animal tissues may also be formed. However, samples may also comprise media from DNA or RNA synthesis or mixtures of chemically or biochemically synthesised DNA or RNA.

In particular, samples include physiological or clinical samples such as blood, urine, milk or saliva, as well as serum or it may comprise tissue extracts, for example plant tissue extracts such as leaf, stem, bark or tuber extracts, or animal tissue (including blood, bone, liver, kidney etc.) or faecal extracts.

Preferably the sample comprises a tissue extract, from an organism such as plant or animal, which may for example be infected by a microorganism and in particular a pathogenic microorganism, or which is required to undergo genetic analysis for typing or other purposes. Extracts are suitably prepared by extracting the sample into a suitable buffer solution. The applicants have found that buffers utilised for extraction of protein samples for use in immunoassays will also extract nucleic acids, and therefore these may be utilised in the present process. The precise buffer solution used in any particular case will depend upon the nature of the sample being tested. However, for the extraction of nucleic acids from plant or animal samples, a suitable buffer solution may comprise a buffer which is readily available such as phosphate buffered saline (PBS) or Tris buffered saline (TBS).

Buffers may suitably comprise preservatives such as sodium azide, formalin or thiomersal. The amount of preservative added in any instance will depend upon the specific preservative used, as well as the type and volume of buffer involved, but for sodium azide for example, it may suitably be added in amount of from 0.2 to 1.5% w/w for example at about 0.5% w/w.

Suitably the tissue sample to be tested is intimately mixed with the extraction buffer, optionally with mechanical disruption means. For example, tissue samples and particularly plant tissue samples have been prepared for immunoassay procedures by placing these into small bottles comprising extraction buffer and ball bearings, and shaking these vigorously so that the ball bearings impact on the sample and assist in the breakdown of the cell structure.

Tissue or other samples may be handled differently, but the precise means of extracting nucleic acids into extracts would be determinable by a person skilled in the art.

Once the sample is applied to the membrane in the sample receiving zone, it is allowed to travel along the membrane as a result of bibulous flow. Depending upon the nature of the sample and the membrane, this procedure can occur rapidly and with minimal operator skill and involvement required.

Thereafter, the membrane, or more suitably a portion of the membrane, for example a small strip or punch extracted from the membrane is taken, for example in a laboratory environment, and utilised for further analysis. This may comprise genetic analysis such as SNP typing or DNA fingerprinting as well as a nucleic acid detection assay, as discussed above.

The portion can be taken from any part of the membrane, but it may be preferable to extract the sample from a region which is spaced from the sample receiving section. This may be particularly relevant in cases where the sample contains for example particularly large proteins or molecules which do not elute well along the membrane and so which can collect in the sample receiving section and inhibit any subsequent detection method such as PCR. Particular samples which may be affected in this way include plant extracts, where large molecules such as chlorophyll tend to collect on the membrane in the region of the sample receiving section on the device.

If desired, the membrane may be marked to indicate a suitable portion size and position. A particular site for extraction of a membrane sample may be in the region of the detection and control zones in a conventional immunoassay LFD. Control lines, which are developed in the course of the assay, in particular by immunoassay techniques, in which labelled may be used to demarcate a sample extraction portion. This provides a further advantage of confirming that the assay has progressed appropriately. The size of the portion of the membrane used in the test may be particularly important if quantitation of nucleic acid is required.

Nucleic acid detection or analysis may be effected using any conventional technique. If necessary or desired, the nucleic acids stored or retained on the membrane can first be washed off the membrane using water or if necessary, eluted off using conventional elution buffer, and the washings or eluate subject to analysis. Washing for 10 minutes at temperatures ranging from ambient temperature to elevated temperature for example up to 100° C. will generally result in the release of the nucleic acid from the membrane.

Preferably however, the analysis is conducted directly on a portion of the membrane.

If it is known in advance, what form the nucleic acid analysis will take, it may be convenient to incorporate one or more reagents useful in that analysis into the membrane, for example in dried form, prior to use. These reagents may either be positioned along the length of the membrane, or, if they are mobile through the membrane but retained at least to some extent thereon, they may be diffusibly located in a sample receiving section or pad on the membrane, so that they are transported with the liquid sample along the length of the membrane.

For example, in order to detect the presence of a specific nucleic acid on the membrane, the membrane or membrane portion is immersed into a PCR mixture. PCR mixtures are well known in the art. They suitably contain reagents such as nucleotides, polymerase and a set of PCR primers that are designed to amplify a specific nucleic acid sequence, which may be characteristic of a particular organism. PCR reactions may further comprise buffers, magnesium salts etc.

If desired, one or more of the reagents necessary for carrying out the PCR may be "preloaded" onto the membrane, either along its length or diffusibly loaded into the sample receiving section or pad on the membrane. In the latter case, suitable "capture" agents such as antibodies or binding fragments of antibodies, which are specific for one or more of these reagents may be immobilised within a portion of the membrane which is intended for later analysis, so as to concentrate these reagents in that portion, ready for latter use. This may be particularly desirable and convenient where the reagent is a polypeptide or protein such as a polymerase enzyme.

Particularly suitable reagents for inclusion in this way include any primers or probes which may be required to perform or detect a specific nucleic acid. By incorporating specific reagents of this type into the membrane, it would be possible to utilise pre-mixed amplification mixtures or moieties, such as PCR ready beads, for the analysis.

Once a PCR mixture has been formed in the presence of nucleic acids on the membrane, it is then subjected to a plurality of thermal cycles, to cause the denaturation of nucleic acids present in the sample, primers to anneal to any target sequence present in the reaction mixture, and then extended by the polymerase, during each cycle.

In a particular embodiment, the PCR reaction is carried out in a quantitative manner. For this purpose, labelled reagents for instance labelled probes and/or DNA binding agents such as intercalating dyes may be included in the PCR reaction. A particular quantitative assay type is the TAQMANT™ assay, in which a probe labelled with two fluorescent moieties which interact with each other by FET or FRET. In the course of the PCR, the probe hybridises to the amplified sequence whereupon the 5' to 3' exonuclease activity of the polymerase digests the probe, thereby separating the fluorescent moieties which fluoresce differently once the physical distance between the moieties increases and so the interaction no longer occurs. The change in fluorescence can be readily detected and thereby the increase in the amount of amplified nucleic acid sequence monitored. By monitoring the change over the amplification cycles, the amount of nucleic acid in the sample can be determined.

In order to relate the amount of nucleic acid present on the membrane to the amount contained within the sample, it may be necessary or desirable to ensure that a precise or measured amount of sample is applied to the membrane initially, and that the size of any portion of the membrane used in the analysis is carefully controlled.

Other quantitative PCR methods are available, for example as described in European Patent No. 1049802B, the content of which is incorporated herein by reference, as well as by the use of Scorpion.™. probes (hypertext transfer protocol ://world wide web. dxsgenotyping. com/technology. hypertext markup language) and Loop-Mediated Isothermal Amplification Method (LAMP) (hypertext transfer protocol ://loopamp.eiken.co.jp/e/index. hypertext markup language).

In a particular embodiment, the invention provides an assay for detecting the presence of a target nucleic acid in a sample, said method comprising the steps of causing a liquid sample suspected of containing said nucleic acid to flow along a membrane for example of a liquid flow device, and detecting the presence of said target nucleic acid on said membrane.

It appears that by effectively "spreading" the nucleic acid over a wide area, the nucleic acids become sufficiently separated from other components in the sample to allow them to be detected using a conventional nucleic acid detection method such as PCR, much more readily and easily than for example would be the case if the sample itself were to be analysed in this way. In effect, it appears that nucleic acids are retained in the membrane structure, and this has a purification effect.

As suggested above, this represents a highly cost effective and efficient method for conducting a simple purification step in any analysis, but in particular for an analysis which involves nucleic acid amplification such as the polymerase chain reaction (PCR) which can be conducted in the presence of membrane material without significant inhibition.

A further advantage of the method described above is that the purification stage could be performed "on-site", for example in field situations, or using kits which can be used either at home or in surgeries including medical and veterinary surgeries. It is necessary to send only the membrane, or the device containing it and not the liquid sample, to the laboratory for analysis, thus virtually eliminating the risk of contamination of laboratory equipment and personnel.

However, portable devices which are able to conduct nucleic acid analyses on site may also be utilised to allow the entire analytical process to be conducted without requiring transport of samples. Such devices are becoming available, but a problem to date has been that the need for complex sample preparation procedures limits their usefulness and portability.

If desired, the membrane, or cassettes, cartridges of the like which are adapted to hold membranes and which may be disposable, may be included in such devices. This will allow rapid and easy purification to be effected in a "field" situation, prior to analysis on site.

The nucleic acid detected as described above can be any desired target nucleic acid. In one embodiment however, it will generally be required to detect nucleic acids which are characteristic of particular pathogenic organisms of plants or animals such as bacteria, viruses or fungi, and in particular those which allow strain typing or serotyping of those organisms.

As discussed above however, the method can be used to purify nucleic acids for any purpose, including sequencing or genetic analysis, including genotyping or SNP analysis. Many of these techniques utilise amplification reactions such as PCR and the method described above can be used in conjunction with any of these.

In a particularly preferred embodiment, the membrane is used in the above-described methods or assays is an element of a liquid flow device which is arranged to carry out an assay for a different analyte, for example immunoassay for a particular polypeptide analyte, for example a protein or peptide analyte, but other analytes such as chemicals for instance pesticides or pesticide residues may comprise the different analyte in this case. The different analyte is may be one which is also indicative of the particular pathogen or condition which is being tested for.

In this way, the immunoassay method can act as a preliminary step in the assay procedure. If the result of the immunoassay step is negative, there may be no need to continue with the more complex nucleic acid detection step. However, if the result is positive, for example indicating the presence of a particular organism type, the second step, of detecting nucleic acid which is characteristic of that organism, will provide confirmation of the result, and may additionally, depending upon the nature of the target nucleic acid sequence, provide further clarification of the nature, species or strain of the organism.

However, it is not necessary for the different analyte and the or each nucleic acid to originate from the same source or organism. For example, it may be desirable for one of the analyte or nucleic acid to be characteristic of a particular infective organism, and the other to be characteristic of a host of said organism. In particular, where the analyte is characteristic of an infective organism, it may be useful to detect a nucleic acid which is found in a gene of the host which impacts on the host's susceptibility or resistance to said organism. For instance, where the different analyte is a pesticide or pesticide residue for example, it may be useful to detect the presence of a gene in the host plant which impacts on the resistance of the host plant to the pesticide.

Further analytes may include for example antibodies to a particular pathogen and so be generated by the host organism. However, nucleic acid analysis looking for nucleic acids which are characteristic either of the pathogenic organism itself, or of an attenuated vaccine strain or sub-unit vaccine, which includes for example a marker sequence, which is then detected, can provide an indication of whether or not an animal has been exposed to disease or vaccinated. The method of the invention allows such combined analysis to be conducted readily and easily, and can lead to information about the vaccination status of an animal. This may be particularly important in the case of diseases such as TB or rabies where the tracking of vaccinated animals is required.

Examples of plant pathogens which may be tested for using the method of the invention for instance include *Phytophthora* spp., which may be a particular pest of for example Rhododendrum plants which it infects the leaves particularly, or PVY which is a particular problem for tobacco leaves, but many other applications are envisaged.

In the field of animal health, veterinary diseases such as foot and mouth disease, swine fever and avian flu may conveniently be detected using this method. In the case of human health issues, bacterial infections such as *E. coli* or *Salmonella* infections and viral infections such as flu, in particular avian flu may be diagnosed using the present method. The method can be designed to detect particular strains of the infecting organism, and this can be very important where the pathogenicity of different strains varies considerably, and where the prognosis or treatment outcomes vary accordingly.

Thus in a further embodiment, the invention provides a two-stage assay for detecting the presence of an analyte and optionally also a nucleic acid in a liquid sample, said method comprising the steps of (i) causing a liquid sample suspected of containing said analyte and nucleic acid to flow along a membrane of a liquid flow device capable of conducting an assay, for example an immunoassay, to detect the presence of said further analyte and, (ii) depending upon the result of step (i), detecting the presence on the membrane of said nucleic acid.

When used in this way, the membrane of the liquid flow device will suitably further comprise a labelled binding agent diffusibly arranged thereon. The labelled binding agent is suitably located in or in the area of the sample receiving zone, so that they are carried along the membrane with the liquid sample.

For instance, the labelled binding agent may be applied to an absorbent pad such as a glass fibre pad which is positioned in the sample receiving zone, and is in liquid contact with the membrane. The labelled binding agent, which for example comprises a latex labelled antibody, or a latex labelled analogue of an analyte is suitably applied to the pad in a buffer solution which contains a strong blocking agent such as a protein blocking agent as discussed below. The buffer may comprise further conventional agents such as protein stabilising agents, viscosity modifying agents or preservatives, particular examples of which are described below.

The pad may also accommodate one or more of the reagents used in the subsequent nucleic acid analysis, such as primers, probes or polymerase, as discussed above.

In addition, the membrane will be provided with a second specific binding agent, immobilised thereon in a detection zone which is "downstream" of the sample receiving zone. As the sample passes down the membrane, any analyte present will interact with either the labelled binding agent and/or the second specific binding agent so as to result in the development of a signal (or lack of signal) in the detection zone which is indicative of the presence or absence of analyte in the sample.

The labelled binding agent and the immobilised second binding agent will specifically bind analyte or each other in accordance with well established immunoassay principles.

For instance, in a so-called "sandwich assay", the labelled binding agent will specifically bind to any analyte in the sample to form a labelled complex. The second binding agent also specifically binds the analyte, so that labelled complex is concentrated in the detection zone giving rise to the development of a visible signal. This sometimes known as a "test line".

In a competitive assay, the labelled binding agent is either a binding partner for said analyte or a labelled analogue of said analyte. In this case, the second binding agent in the detection zone specifically binds the labelled binding agent in competition with the analyte. Thus for example, where the labelled binding agent is a labelled binding partner for said analyte, an analogue of the target analyte is immobilised in the detection zone. As the sample passes the detection zone, any free labelled binding agent (i.e unbound to analyte) will associate with the immobilised binding agent and a visible signal will develop. However, if analyte is present in the sample, it will bind to the labelled binding partner before the detection zone is reached, and thus prevent this binding. Therefore, the absence of a signal in the detection zone is indicative of the presence of analyte in the sample.

Similarly, where the labelled binding agent is labelled analogue of said analyte, the second immobilised binding agent is a binding partner for said analyte and the labelled analogue of the analyte. In this case, both analyte and labelled analogue will compete for binding sites in the detection zone. Signal will only arise as a result of binding of the labelled analogue, and so in this instance, again, the more analyte present, the less signal will be accumulated in the detection zone.

As used herein, the expression "analogue of the analyte" refers to a moiety which behaves in a similar manner to the analyte in the context of the assay system. Hence, it may comprise the analyte itself, or a variant or fragment of the analyte, such as an epitopic fragment, which will interact with specific binding agents used the assay as the analyte itself would.

The applicants have found that a liquid flow device can not only provide a rapid and easy method for detecting specific proteins in a sample, but that the conditions to which the sample is subjected appears to be a useful means of capturing nucleic acid in a form in which it may be readily detected for example using a nucleic acid amplification method such as the polymerase chain reaction or "PCR". By combining these two techniques, significant advantages can arise.

The label used on the labelled binding reagent is preferably a visible label which can be used to give a signal which is readable either using the naked eye or using a reflectance reader, and most preferably a portable or desktop reflectance reader. Examples of such labels, particulate labels such as latex, gold and silica.

Other visible labels such as fluorescent or chemiluminescent labels that may be detected using a fluorimeter or luminometer respectively may be employed.

Alternatively, the labels may comprise radioactive, labels that may be detected using a radiation detector.

However, as discussed above, the method of the invention is applicable in the absence of any visible detection means for the analysis or detection of nucleic acids.

Membranes suitable for use in the methods described above, such as those used in liquid flow devices and in particular nitrocellulose membranes are naturally hydrophobic, which gives rise to the necessary wicking effect. However, the hydrophobicity can give rise to problems when these are used in the context of a conventional immunoassay procedure in that The membranes used in these devices are suitably blocked using conventional blocking agents. Blocking agents are those which may reduce non-specific interactions between any protein in the sample and the membrane or increase the wicking rate of the sample. They are generally applied after the application of immobilised binding agents and are usually selected from three types of agent including proteins, surfactants and synthetic polymers.

Particular examples of proteins which may be used as blocking agents include bovine serum albumin (BSA), of non-fat dry milk components such as casein.

Examples of surfactants which may be used as blocking agents include non-ionic surfactants such as polyoxyethylene sorbitan monolaureate which is sold under the trade name of Tween™ 20 and octylphenol ethoxylates for example as sold by Dow as the Triton X™ series, for example Triton X-100.

Suitable synthetic polymers for use as blocking reagents include polyvinyl alcohol (PVA), polyvinylpyrroline (PVP), polyethylene glycol (PEG) and polyoxyethylene fatty ethers such as those derived from lauryl, cetyl, stearyl and oleyl alcohols and sold under the trade name Brij™. Molecular weights of these polymers will vary depending upon the nature of the polymer used, but will generally be in the range of from 5-50 kDa, for example from 8-15 kDa.

It is generally recognised that mixtures of two or more of these types or classes of blocking reagent may be particularly employed, for example a mixture comprising a surfactant and a synthetic polymer as outlined above.

The presence of certain blocking agents such as those outlined above may do not appear to impede the purification of the nucleic acids, as noted by the applicants.

The applicants have found that a conventionally blocked membrane as described above is also suitable for non-specific binding of nucleic acids. Thus it is possible to prepare membranes for immunoassay purposes and retain the advantages of the present invention.

Blocking reagents are conventionally applied to the membrane in the form of a buffer solution, which is then allowed to dry before use. The applicants have found that suitable buffers have pHs in the range of from 8 to 9, and preferably about 8.5. A wide variety of buffers having this property would be apparent to a skilled person. Conventional buffers, for example those based upon Tris, phosphates, potassium hydrogen phthalate, sodium borohydrate, or potassium or sodium bicarbonates which an acid or base as appropriate may be included and these do not appear to reduce the retention of the nucleic acid.

Additionally or alternatively, blocking agents may be combined with the labelled reagents so as to ensure that they are diffusible along the membrane.

The buffer solution used to apply the blocking reagent to the membrane or to apply the labelled reagent to the sample delivery region may suitably additionally comprise a protein stabilising agent such as sucrose or trehalose. These may also modify the viscosity of the buffer solution to a sufficient extent to allow the blocking agent to become bound to the membrane on simple immersion therein. The amount of stabilising agent included in the buffer varies depending upon the nature of the buffer and the precise nature of the stabilising or viscosity modifying agent.

Once again, if required, a preservative such as those outlined above for the extraction buffer may be added to the buffer containing the blocking agent.

If desired, the immunoassay may comprise additional reagents or components as would be understood in the art. For example, there may be a binding partner for the labelled binding agent immobilised in a "control" zone, which is suitably located downstream of the detection zone. Any residual labelled binding agent will bind in this second zone, suitably to produce a "control line" which is indicative of satisfactory flow of labelled binding agent. Alternatively, specific labelled control reagent may be added diffusibly onto the membrane, for example in admixture with the first labelled binding agent, and a specific binding agent for the labelled control reagent immobilised in the control zone to give rise to a control line, allowing confirmation that the immunoassay has proceeded satisfactorily.

If desired, the immunoassay can be carried out using a quantitative or semi-quantitative method as outlined for example in WO2006003394, the content of which is incorporated herein by reference.

A study was set up to determine whether it was possible to amplify a signal using PCR from a positive test line on an LFD strip. It was anticipated that it could be useful to have this ability in order to confirm a positive LFD result by excising the test line and performing PCR in the laboratory. It was further anticipated that this technique would make it possible to distinguish between strains or species of target present in the sample where the LFD test is unable to do so, for example in the case of *Phytophthora* or avian flu assays.

Results from a particular study reported below showed that it is indeed possible to confirm the result from the test line by PCR. The results further showed that it is possible to perform a positive PCR analysis from DNA taken from any domains on a used LFD strip. Domains upstream and downstream of the test line were successfully tested.

Furthermore, the Ct values obtained from PCR analysis of DNA from the LFD membrane were equivalent to those from analyses using standard complex purification and/or storage methods. This suggests that the extraction buffer and/or membrane treatment systems used in the LFD analysis is working to purify the DNA and remove contaminants/inhibitors as effectively as standard methods.

As outlined further below, existing technology and expertise was used to develop a lateral flow device (LFD) based upon the standard sandwich assay format, the principle of which relies upon the capture of target between an immobilised line of target specific antibody on nitrocellulose membrane (Test line) and a coloured latex-antibody conjugate (anti-target mouse antibody) to display a visible confirmation of target presence. A line of anti-mouse antibody was incorporated into the device to provide visual verification of latex flow (Control line), resulting in two lines as an indication of positive detection and a single line for a negative result. Latex conjugate was applied onto a glass fibre release pad to produce a stable particle reservoir, and assembled together with the membrane and an absorbent pad into a protective plastic housing.

The addition of 75 µl (approx. two to three drops) of sample extract onto the sample well released latex conjugate onto the membrane, which began to flow towards the absorbent pad. If target antigen was present in the sample extract, antibody binding occurred to produce a latex-antigen complex, which was in turn captured by the test line; thus producing a visible line of deposited latex. The anti-mouse antibody captured any excess latex conjugate, providing a visible confirmation of latex flow.

Subsequent analysis of samples of the membrane along its length by a real-time PCR assay showed that nucleic acid characteristic of a particular species of the target organism (in this case *Phytophthora ramorum*) was detectable along the length of the membrane. Further analysis of the membrane revealed that it also contained COX DNA which is derived from host Rhododendron.

As outlined above, it may be envisaged that in general, in use, any immunoassay element of the test may be conducted in a field situation, and the liquid flow device, once used, provides a convenient means of transporting nucleic acids to a laboratory environment for further analysis. However, kits may be prepared to conduct the assay.

Thus in a further aspect, the invention provides a kit for conducting an assay according to any one of the preceding claims, which comprises a bibulous membrane, for example one which forms an element of a liquid flow device, and at least one reagent used in the detection of nucleic acids.

Suitable reagents used in the detection of nucleic acids include one or more primers suitable for amplification of a target nucleic acid sequence, but other reagents may include probes in particular fluorescently labelled probes such as those utilised in the TAQMAN™ assay which will be specific for the target nucleic acid, as well as enzymes such as DNA polymerase, buffers, salts etc.

Suitably the liquid flow device is arranged to conduct an immunoassay to detect an analyte, in particular a polypeptide analyte which is derived from the same species as the target nucleic acid. It may take a sandwich or competitive assay format as discussed above.

The invention will now be particularly described by way of example, with reference to the accompanying diagrammatic drawings in which.

Figure 1:
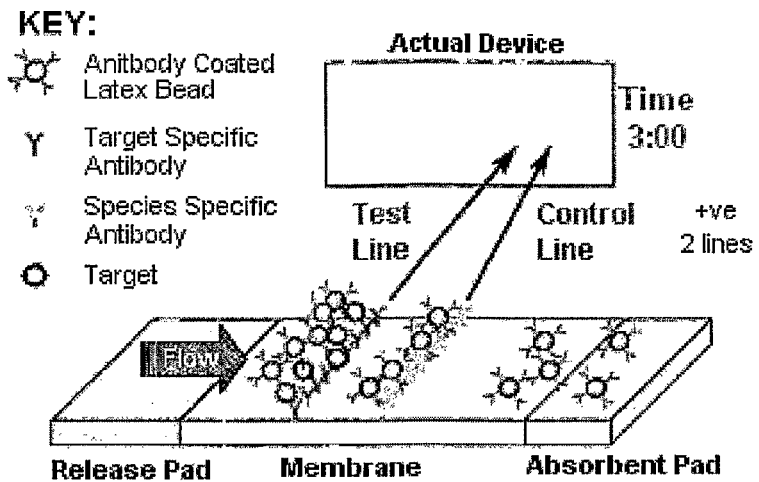
FIG. 1 illustrates schematically a liquid flow device which may be used in the method of the invention.
Figure 2:
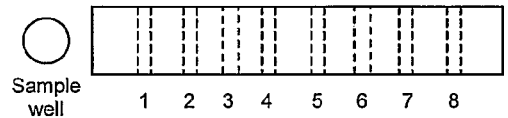
FIG. 2 illustrates a membrane sampling regime which may be used in the method of the invention.
Figure 3:
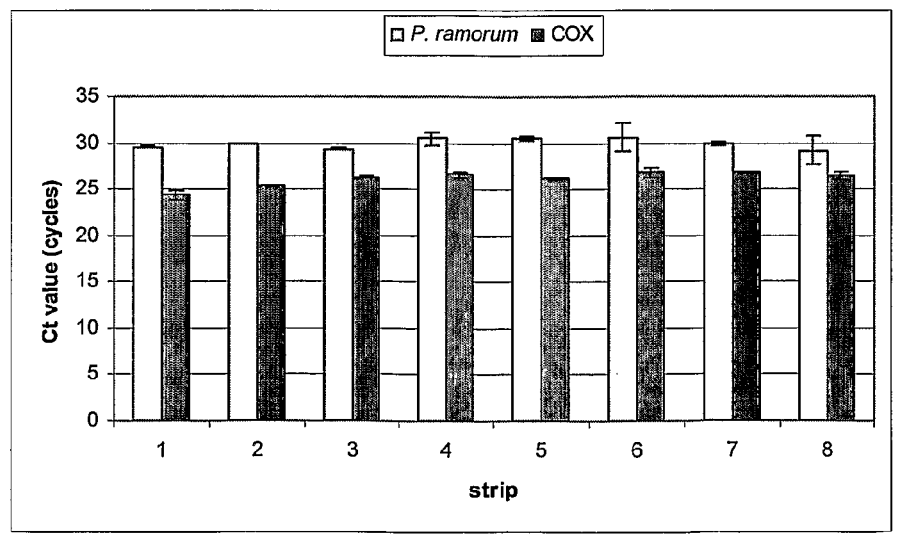
FIG. 3 illustrates the results of a PCR reaction carried out in an embodiment of the invention.
Figure 4:
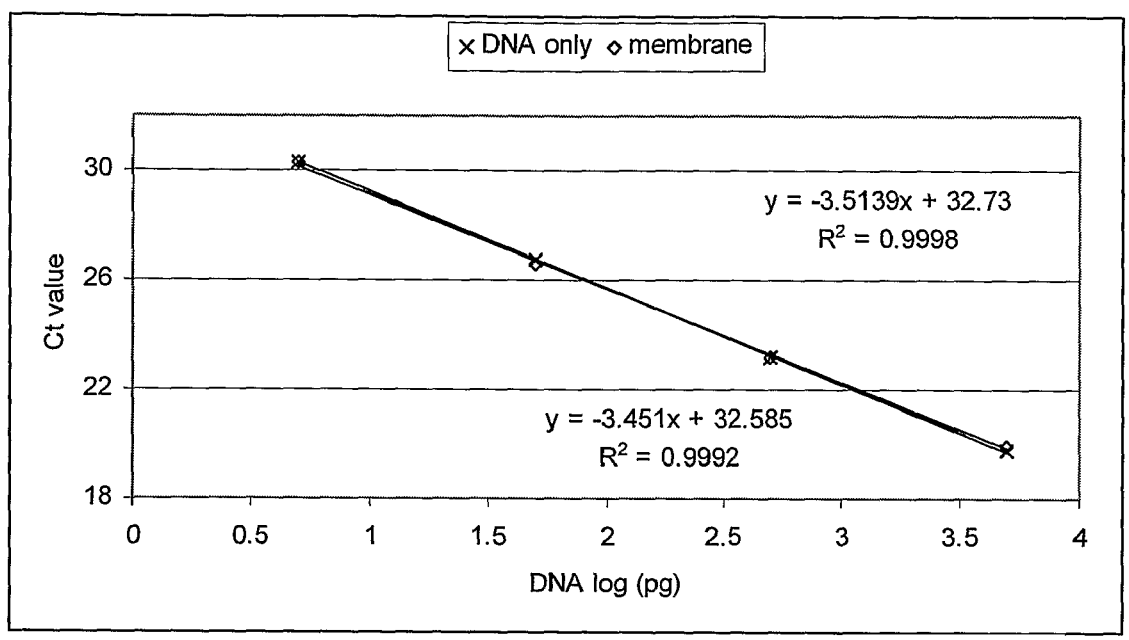
Figure 5:
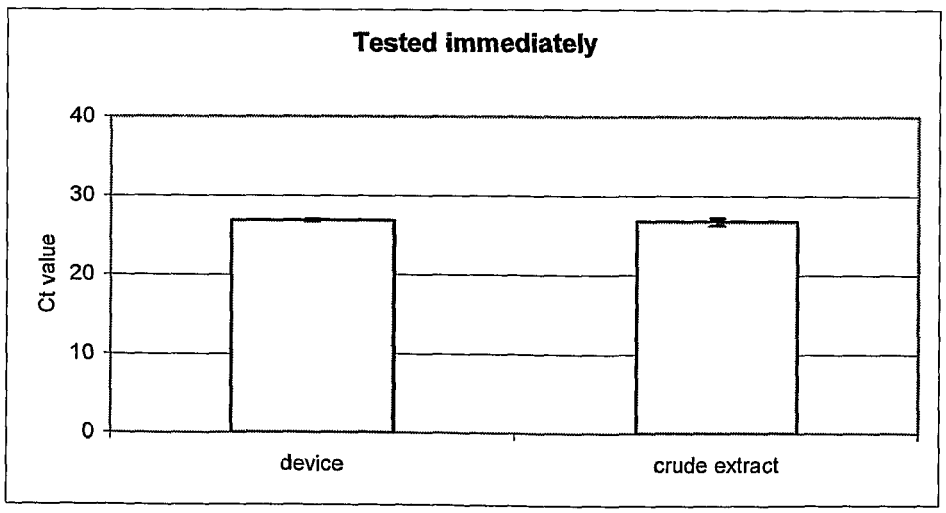
Figure 6:
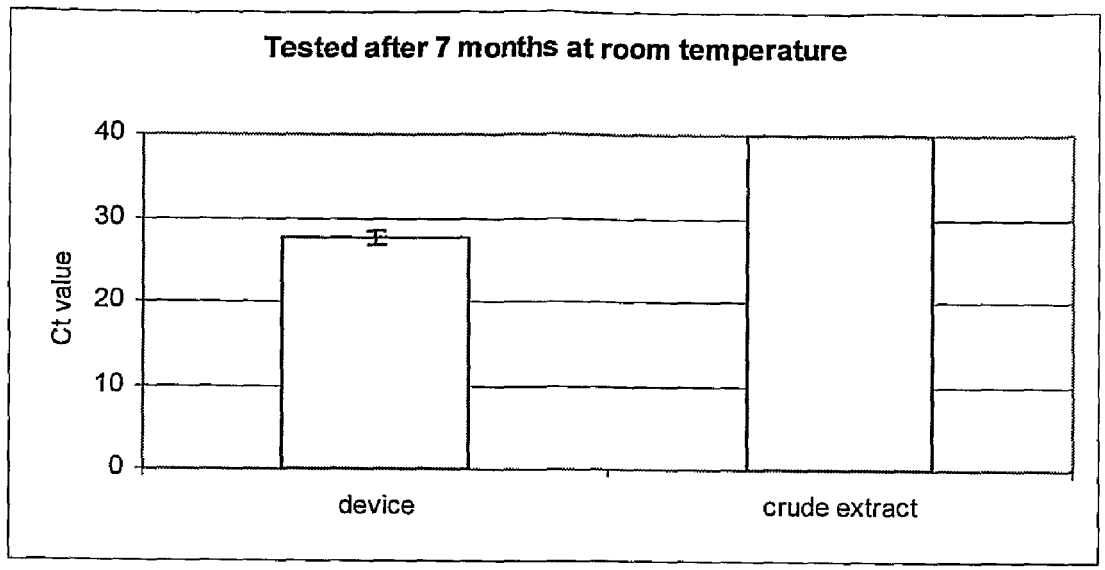
Figure 7:
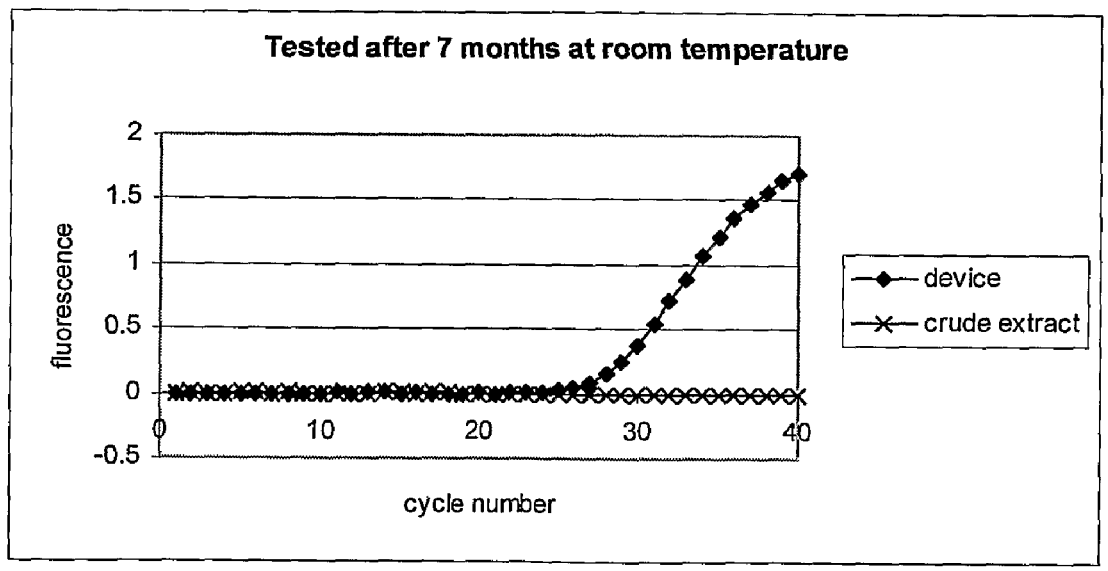
Figure 8:
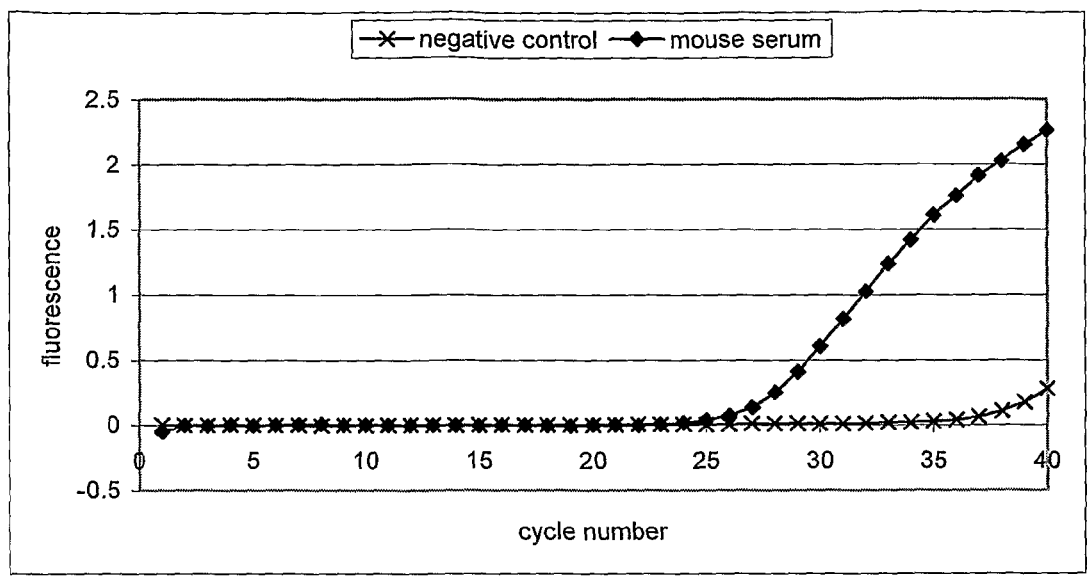
Figure 9:
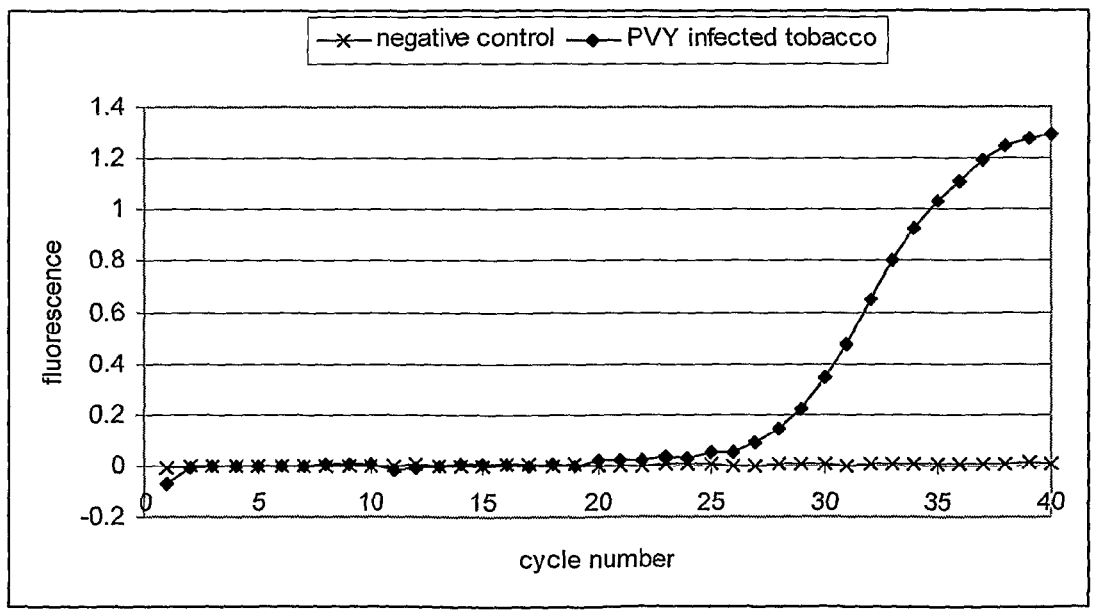
Figure 10:
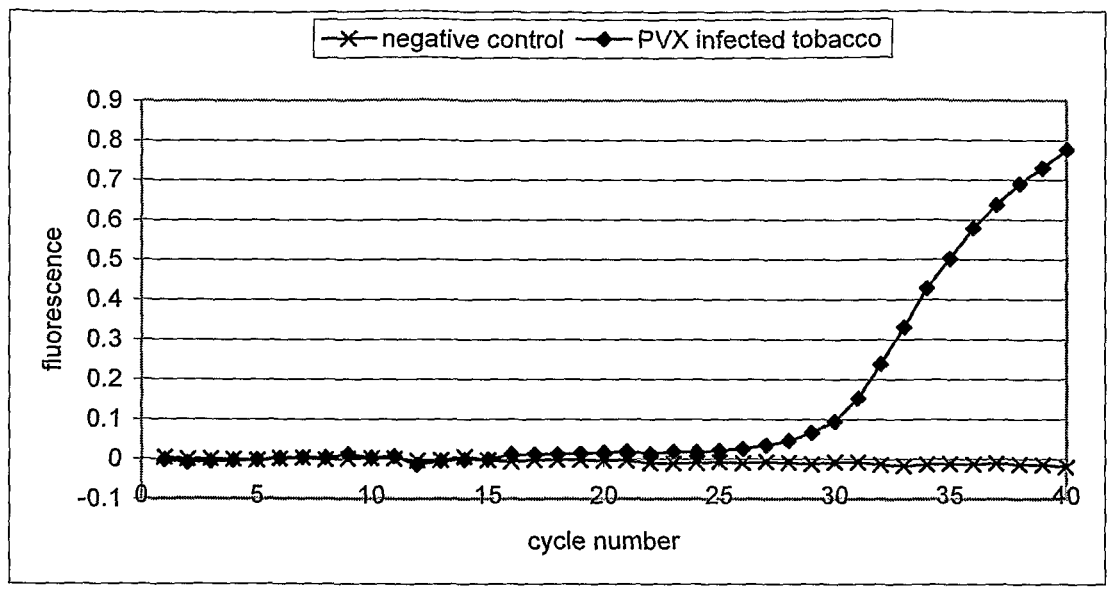
Figure 11:
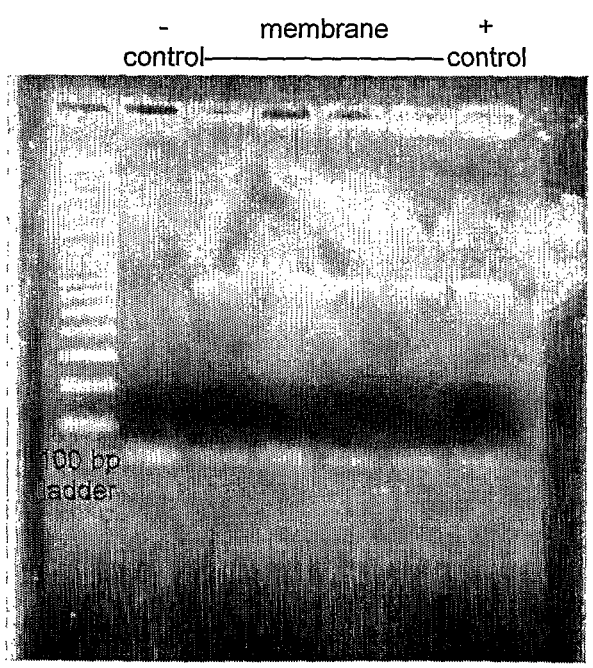

FIG. 4 is a graph showing Ct values for a TaqMan™ amplification of a dilution series of extracted *P. ramorum* DNA as compared to that carried out on a membrane from an LFD along which a sample of a crude extract from a *Phytophthora ramorum*-infected *rhododendron* sp. has been run;

FIG. 5 is a graph showing the Ct values for the same assay as that used in relation to FIG. 4 but on the crude extract itself directly after preparation taken (crude extract), as well as on a membrane of an LFD treated with the crude extract directly after preparation (device);

FIG. 6 is a graph showing a similar comparison of Ct values to that shown in FIG. 6 carried out on the same crude extract and membrane but after storage at room temperature for 7 months;

FIG. 7 is a TaqMan amplification plot of the results shown in FIG. 6;

FIG. 8 is an amplification plot for TaqMan™ detection of 18S rRNA in normal mouse serum; negative control=water;

FIG. 9 shows an amplification plot for TaqMan™ detection of PVY in inoculated tobacco;

FIG. 10 shows an amplification plot for TaqMan™ detection of PVX in inoculated tobacco;

FIG. 11 shows a gel obtained following a conventional PCR reaction for *P. ramorum.*

EXAMPLE 1

*Phytophthora ramorum* Detection

A sample of *Phytophthora ramorum*-infected *rhododendron* sp. leaf (1-2 $cm^2$) was cut into small pieces using a scalpel blade, placed in an LFD extraction bottle, of an LFD kit obtained from Pocket Diagnostics™ (CSL, York, UK) containing extraction buffer.

The bottle was shaken for approximately 2 minutes, then 2 drops of the sample were transferred to the sample well of a *Phytophthora* spp. LFD contained within the kit. The LFD in this case comprises a conventional sandwich assay format as illustrated in FIG. 1.

Once the sample had been absorbed, the membrane was removed from the plastic housing and eight 1-2 mm wide strips were cut from along the length of the membrane (FIG. 2). Each strip was cut in half, and each half strip was placed in a separate well of a 96-well plate containing 25 μl master-mix for multiplex real-time PCR (Taqman) for *P. ramorum* and COX (1×PCR buffer (50 mM KCl, 10 mM Tris-HCl, 0.001% gelatin), 0.025 U/μl Hot Taq, 0.2 mM each dNTP, 5.5 mM $MgCl_2$, 1×ROX passive reference dye, 300 nM each *P. ramorum* primer, 200 nM each COX primer and 100 nM each *P. ramorum* and COX probes).

Real-time PCR was carried out on an ABI 7900HT, with cycling conditions of 10 min at 95° C. followed by 40 2-step cycles of 15 s at 95° C. and 1 min at 60° C.

Results

*P. ramorum* and COX Ct values for each strip are shown in FIG. 3 (error bars show standard deviations for replicate reactions (two halves of each strip)). Very similar Ct values were obtained using a PVY LFD (data not shown).

The Ct values indicate that both host DNA (COX) and target DNA (*P. ramorum*) could be identified from the LFD membrane irrespective of sample location. The results using a *P. ramorum* sample on a PVY LFD were very similar indicating that the specificity of the LFD, i.e. specific monoclonal antibodies, are not critical to nucleic acid extraction.

EXAMPLE 2

PVY Analysis

A potato virus Y (PVY) LFD, prepared as described above in Example 1 except using antibodies specific for PVY antigens, which had been exposed to a plant (potato) extract infected with PVY, (and therefore showed a positive result) was stored at ambient temperature in a sealed plastic bag for in excess of 6 years. The membrane was removed from the LFD and several 1-2 mm wide strips were cut from it. Each strip was cut in half, and each half strip was placed in a separate well of a 96-well plate containing 25 μl master-mix for either real-time RT-PCR (Taqman) for PVY (1×PCR buffer (50 mM KCl, 10 mM Tris-HCl, 0.001% gelatin), 0.02 U/μl M-MLV reverse transcriptase, 0.025 U/μl Hot Taq, 0.2 mM each dNTP, 5.5 mM $MgCl_2$, 1×ROX passive reference dye, 300 nM each PVY primer and 100 nM PVY probe), or real-time PCR (Taqman) for the plant cytochrome oxidase (COX) gene (1×PCR buffer, 0.025 U/μl Hot Taq, 0.2 mM each dNTP, 5.5 mM $MgCl_2$, 1×ROX passive reference dye, 300 nM each COX primer and 100 nM COX probe). Real-time PCR was carried out on an ABI 7900HT, with cycling conditions of 30 minutes at 48° C., then 10 min at 95° C. followed by 40 2-step cycles of 15 s at 95° C. and 1 min at 60° C.

Results

PVY and COX were successfully detected by RT-PCR and PCR respectively. PVY and COX Ct values are shown in Table 1.

| | Ct values (2 replicate reactions) |
|---|---|
| PVY (RNA target) | 28.56, 26.14 |
| COX (DNA target) | 31.54, 31.45 |

This result indicates that the lateral flow device or LFD has retained nucleic acid in a stable manner over an extended period of time.

Similar good results were obtained with fresh samples of PVY and also on a real-time assay carried out on PVX (see FIGS. 9 and 10 respectively).

EXAMPLE 3

Effect of Membranes/LFD

The experiment described in Example 1 was repeated for the detection of *P. ramorum* using an extract of *P. ramorum* innoculated rhododendron as the sample, as range of different commercially available membranes as follows:

1 Millipore Corp. HiFlow 180
2 Millipore Corp. HiFlow 135
3 Millipore Corp. HiFlow 120
4 Millipore Corp. HiFlow 90
5 Millipore Corp. HiFlow 75
6 Millipore Corp. HiFlow 65
7 Schleicher & Schuell Prima 40

Each membrane was treated with a conventional blocking solution utilised in LFD production, and with or without a conventional buffer used to apply the latex labelling system of a conventional LFD. In a later experiment, membrane samples Millipore Corp. HiFlow 75 and Millipore Corp. HiFlow 180 which were untreated were also used.

A range of commercially available LFD was also subjected to treatment as described in Example 1. These included the "Clearblue™" pregnancy test kit, Tesco home pregnancy test kit, a commercially available kit for detecting avian influenza virus available from Anigen and Cucumber Mosaic Virus (CMV) ImmunoStrip produced by Agdia. Some of these kits used gold labels as the protein signalling mechanism and others used latex.

*P. ramorum* nucleic acid was successfully detected in samples taken from all membranes and the LFDs listed above, irrespective of the pore size or the presence or absence or nature of the pre-treatment regime of the membrane.

EXAMPLE 4

Comparison with Pure DNA Detection

A sample of pure *P. ramorum* DNA was subjected to a TaqMan™ assay for the detection of *P. ramorum* as described in Example 1 along with a membrane from an LFD treated with a crude extract of healthy rhododendron to which *P. ramorum*, also as described in Example 1. The sample was then spiked with an equivalent amount of *P. ramorum* DNA before the TaqMan™ was conducted. The results are shown in Table 1 and illustrated in FIG. 4 hereinafter.

TABLE 1

| | slope | Amplification efficiency |
|---|---|---|
| DNA only | −3.5139 | 0.93 |
| membrane | −3.451 | 0.95 |

(Efficiency is calculated from the slope of the standard curve as $10^{(-1/slope)}-1$)).

It is clear from these results that the presence of the membrane has a negligible effect on the efficiency of the amplification reaction. Furthermore, the presence of rhododendron DNA did not inhibit the efficiency of the assay in any way.

EXAMPLE 5

Storage Experiment

A crude extract as described in Example 3 was subjected to a TaqMan assay as described in Example 1 directly after preparation. It was also applied to an LFD as described in Example 1, and the membrane from the device subjected to a similar assay as soon as it had run. The results (FIG. 5) show that, immediately after preparation, both samples gave positive results.

Both the crude extract and the membrane were then stored at room temperature for 7 months and the analysis repeated. The results are shown in FIG. 6 and FIG. 7 which is a TaqMan amplification plot of the results shown in FIG. 6.

These results show that the membrane acts as an effective nucleic acid storage mechanism.

EXAMPLE 6

Detection of Nucleic Acids in Other Sample Types

Mouse serum was added to an LFD, and allowed to run along it. Once the sample had been absorbed, the membrane was removed from the plastic housing, and subjected to a TaqMan real-time PCR assay designed to detect eukaryotic 18S rRNA gene. This is a pre-developed endogenous control assay available from Applied Biosystems. A negative control (water) was also applied to a second LFD.

The results are shown in FIG. 8. Clearly serum is a suitable sample type for use in connection with the present method.

[The 18S rRNA gene is found in all eukaryotes, which probably explains the slight contamination in the negative control).

EXAMPLE 7

Different Detection Methods

A range of different assays were conducted in which samples were run along the membranes of LFD devices as described in Example 1 and nucleic acid present in those samples then detected using either real-time PCR, specifically the TaqMan assay, or conventional PCR as well as the LAMP assay.

TaqMan PCR reactions typically contain 1×Applied Biosystems Buffer A (50 mM KCl, 10 mM Tris-HCl pH 8.3, carboxy-X-rhodamine (ROX) passive reference dye), 0.025 U/μl Applied Biosystems AmpliTaq Gold, 0.2 mM each dNTP, 5.5 mM $MgCl_2$, 300 nM each primer and 100 nM TaqMan probe. TaqMan Reverse transcriptase PCR (RT-PCR) for detection of RNA viruses also contain 0.02 U/μl M-MLV reverse transcriptase. Cycling conditions were 10 min at 95° C. followed by 40 2-step cycles of 15 s at 95° C. and 1 min at 60° C. This was preceded by a reverse transcription step of 30 min at 48° C. from RT-PCR. Real-time PCR was carried out on an ABI 7900 HT.

Results are interpreted in terms of Ct value ie the cycle at which fluorescence exceeds a threshold value.

LAMP reactions contain 0.32 U/μl Bst DNA polymerase (New England Biolabs, Ipswich, Mass.), 1×Thermopol buffer, 1.4 mM each dNTP, 6 mM $MgCl_2$ (including 2 mM in Thermopol buffer), 1.2 M betaine, 200 nM each external primer (F3 and B3), 2 μM each internal primer (FIP and BIP), and 1 μM each loop primer (F-Loop and B-Loop). Reactions were incubated at 65° C. for 40 minutes, then at 80° C. for 5 minutes to inactivate the Bst polymerase. Amplified products were visualized by adding 2 μl Quant-iT PicoGreen dsDNA reagent (Invitrogen, Carlsbad, Calif.) and observing the colour change (from orange to yellow).

PCR reactions contain 1×Fermentas PCR Buffer (10 mM Tris-HCl (pH 8.8 at 25° C.), 50 mM KCl, 0.08% (v/v) Nonidet P40.), 0.025 U/μl Fermentas Taq polymerase, 0.2 mM each dNTP, 2 mM $MgCl_2$, 500 nM each primer. Cycling conditions were 2 min at 95° C. followed by 30 3-step cycles of 30 s at 95° C., 30 s at 57° C., and 30 s at 72° C. Products were visualized by gel electrophoresis (1.2% agarose gel) followed by staining with ethidium bromide (FIG. 11).

In all cases, successful detection of nucleic acids on the membrane was found.

The assays and the amplicon sizes are summarised in Table 2

TABLE 2

| Assay | Amplicon (base pairs) |
|---|---|
| COX TaqMan | ~79 |
| P. ramorum TaqMan | 77 |
| PVY TaqMan | 67 |
| PVX TaqMan | 71 |
| P. ramorum conventional PCR | ~700 |
| A. tumefaciens TaqMan | 60 |
| 18S rRNA TaqMan | <80 |
| P. ramorum LAMP | 240 |

A wide range of different amplicon sizes was detected on the membranes, indicating that the size of the nucleic acids is not important in determining whether or not they are retained on the membrane.

EXAMPLE 8

Testing of East African Rose Material for the Presence of the Crown Gall Pathogen, Agrobacterium tumefaciens, by Extracting DNA onto LFDs and Whatman FTA Cards and Subsequent Real-Time PCR Rose crops throughout East Africa have recently been severely affected by a disease known as crown gall. This disease is caused by strains of the bacterium Agrobacterium tumefaciens which harbour a small-circular piece of DNA known as a Ti-plasmid. As these plasmids are harboured internally by the bacterium, and also because many avirulent Agrobacterium strains exist in nature, the only way of detecting the pathogen is by isolating bacterial DNA and then testing this DNA for the presence of the Ti-plasmid.

A recent trip to Kenyan rose nurseries was undertaken. Samples from affected rose plants were taken and administered to both an LFD based upon a Millipore Hiflow 75 membrane and also to Whatman FTA cards. These were then transported to the UK for testing using either a Ti-plasmid specific real-time PCR assay, known as the T-DNA assay which detects the Agrobacterium pathogen, or the COX plant DNA real-time PCR assay, which is used as an internal control to ensure the DNA extraction process has worked.

Processing of Membranes (a) LFD device. Two×1.25 mm diameter discs were taken from each inoculated LFD membranes using a Harris Unicore Hole Punch. These discs were placed directly into one well of a 96-well PCR plate. After sampling all membranes 25 µL of real-time PCR mastermix was added to each well which contained discs. PCR plates were briefly centrifuged to ensure that both discs and mastermix were located at the bottom of each well. The plate was then placed directly in a real-time PCR machine and the cycling reaction was initiated.

(b) Whatman FTA cards. Two×1.25 mm diameter discs were taken from each inoculated FTA card using a Harris Unicore Hole Punch. These discs were placed directly into one well of a 96-well PCR plate. After sampling all membranes 200 µL of Whatman purification buffer was added to each well and the plates incubated at room temperature for 5 minutes. After 5 minutes the buffer was removed from each well, taking care to ensure the discs remained in the wells. This purification step was repeated two more occasions. After the third purification step 200 µL of 1×TE buffer was added to each well and the plates incubated at room temperature for 5 minutes. After 5 minutes the buffer was removed from each well, taking care to ensure the discs remained in the wells. This step was repeated one more time. After the last aliquot of 1×TE buffer was removed from the wells the plates were dried, using a PCR machine heat block, at 56° C. for 20 minutes. Once the discs were dry then 25 µL of real-time PCR mastermix was added to each well which contained discs. PCR plates were briefly centrifuged to ensure that both discs and mastermix were located at the bottom of each well. The plate was then placed directly in a real-time PCR machine and the cycling reaction was initiated.

Results

Samples were taken from various different points of rose plants. It was found that stem sections, specifically the graft union where the flowering variety is fused to a root stock variety, was the most likely place to detect the crown gall pathogen as the wound created by this union attracts pathogenic Agrobacterium spp. and thus the pathogen congregates at this point.

The results presented below are from ten different 1-2 cm stem sections, macerated and applied to both devices using the buffer supplied in the 2 minute DNA kit bottles. Four of these samples were taken across a graft union.

TABLE 3

Results from the T-DNA and COX real-time PCR assays from 10 rose stem sections.

| | Real-time PCR results and $C_T$ values | | | |
|---|---|---|---|---|
| | LFD kit samples | | Whatman FTA card samples | |
| Sample | T-DNA PCR | COX-PCR | T-DNA PCR | COX-PCR |
| Stem 1 | Negative | +ve (25.62) | Negative | +ve (24.47) |
| Stem 2 | Negative | Negative | Negative | Negative |
| Stem 3 | Negative | +ve (25.82) | Negative | +ve (32.86) |
| Stem 4 | Negative | Negative | Negative | +ve (30.44) |
| Stem 5 | Negative | +ve (27.56) | Negative | Negative |
| Stem 6 | Negative | +ve (27.63) | Negative | +ve (27.10) |
| Stem 7 (GU)[1] | +ve (34.75) | +ve(26.74) | +ve (37.11) | +ve (27.98) |
| Stem 8 (GU) | +ve (39.51) | +ve (27.35) | Negative | +ve (27.09) |
| Stem 9 (GU) | +ve (39.81) | +ve (26.82) | +ve (39.63) | +ve (26.40) |
| Stem 10 (GU) | Negative | +ve (25.46) | Negative | +ve (26.58) |

[1](GU) - stem section incorporating a graft union

This shows that the results obtainable from the method of the invention are at least as good if not better than those obtained using a Whatman FTA card. The method was however much more simple to operate as is clear from the protocols described.

Furthermore, the use of an LFD provides the additional advantage that a preliminary protein diagnostic assay may be conducted at the same time.

The invention claimed is:

1. A method for separating nucleic acid from other components in a crude liquid sample, said method comprising the steps of applying a liquid sample containing or suspected of containing said nucleic acid to a sample receiving section of a bibulous membrane which does not carry any specific binding agents for nucleic acids, causing said liquid sample to flow along the bibulous membrane, so that nucleic acid is distributed along the length of the membrane and sufficiently separated from other components in the liquid sample to allow detection thereof and thereafter, detecting nucleic acid on or recovering nucleic acid from a region of said membrane which is spaced from the sample receiving section.

2. A method according to claim 1 further comprising the step of drying the membrane after the liquid has flowed along it.

3. A method according to claim 2 further comprising the step of storing the dried membrane.

4. A method according to claim 1 further comprising subjecting separated nucleic acid to further analysis.

5. A method according to claim 4 wherein the further analysis is conducted using a sample of the membrane.

6. A method according to claim 4 wherein nucleic acid is eluted from the membrane prior to said further analysis.

7. A method according to claim 4 wherein the further analysis comprises SNP typing, DNA fingerprinting or sequencing.

8. A method according to claim 4 wherein a specific target nucleic acid is detected.

9. A method according to claim 4 wherein the membrane is a nitrocellulose membrane.

10. A method according to claim 4 wherein the membrane is an element of a liquid flow device.

11. A method according to claim 10 wherein the liquid flow device comprises a sample receiving section and an absorbent section arranged remotely from the sample receiving section on the membrane.

12. A method according to claim 1 wherein the membrane is accommodated within a solid housing or the membrane is laminated.

13. A method according to claim 1 wherein the membrane is processed so as to enhance the wicking of liquid therealong.

14. A method according to claim 1 wherein the sample is a physiological or clinical sample or a tissue extract.

15. A method according to claim 11 wherein the sample is an extract of a plant or animal tissue.

16. A method according to claim 11 wherein the sample is blood, serum, urine, milk or saliva or a faecal extract.

17. A method according to claim 1 wherein the sample is an environmental sample.

18. A method according to claim 17 wherein the sample is a water sample or a soil extract.

19. A method according to claim 1, wherein said nucleic acid is a target nucleic acid and said detecting comprises detecting the presence of the specific target nucleic acid.

20. A method according to claim 1 wherein a section of the membrane is taken after the sample has been allowed to run along it, and the presence of nucleic acid detected thereon.

21. A method according to claim 20 wherein the nucleic acid is detected using a nucleic acid amplification reaction.

22. A method according to claim 21 wherein a reagent useful in said nucleic acid amplification reaction is present on the membrane after the sample has flowed therealong.

23. A method according to claim 22 wherein the said reagent is present on the membrane before the application of the sample.

24. A method according to claim 22 wherein the said reagent is present in a sample receiving section, and is transferred along the membrane in conjunction with the sample.

25. A method according to claim 22 wherein the said reagent is an amplification primer.

26. An method according to claim 21 wherein the amplification reaction is a polymerase chain reaction (PCR).

27. A method according to claim 26 wherein the progress of the PCR is monitored in real-time.

28. A method according to claim 27 wherein amount of sample applied to the membrane is known and the results of the monitoring are used to quantitate the amount of nucleic acid present.

29. A method according to claim 1 wherein the presence of more than one nucleic acid one the membrane is detected.

30. A method according to claim 29 wherein multiple PCR reactions are conducted using the same or different samples of the membrane.

31. A method according to claim 29 wherein a multiplex PCR reaction is conducted to allow more than one nucleic acid to be detected in a single PCR.

32. A method according to claim 1 wherein more than one nucleic acid is recovered from the membrane.

33. A method according to claim 1 wherein the membrane further comprises at least one immunologically reactive reagent for conducting an immunoassay of said liquid sample.

34. A method according to claim 33 wherein the at least one immunologically reactive reagent comprises antibodies.

35. A method of claim 33 further comprising detecting the presence or absence of an immunologically reactive analyte in said liquid sample by said immunoassay.

36. A method according to claim 33 wherein the membrane further comprises a labelled binding agent diffusibly arranged thereon.

37. A method according to claim 35 wherein the said analyte and nucleic acid originate from the same organism, or a particular species of the same organism or a particular genotype of the same organism.

38. A method according to claim 37 wherein the analyte is characteristic of a type of organism, and the nucleic acid is characteristic of a particular species of said organism.

39. A method according to claim 35 wherein one of the analyte or nucleic acid is characteristic of a particular infective organism, and the other is characteristic of a host of said organism.

40. A method according to claim 39 wherein the analyte is characteristic of an infective organism, and the nucleic acid is found in a gene of the host which impacts on the host's susceptibility or resistance to said organism.

41. A method according to claim 35 wherein the analyte is a pesticide applicable to a plant and the nucleic acid is found in a gene of the plant.

42. A method for separating nucleic acid from other components in a liquid sample, said method comprising the steps of applying a liquid sample containing or suspected of containing said nucleic acid to a sample receiving section of a bibulous membrane which does not carry any specific binding agents for nucleic acids, causing said liquid sample to flow along the bibulous membrane, so that nucleic acid is distributed along the length of the membrane and sufficiently separated from other components in the liquid sample to allow detection thereof and thereafter, drying and storing said membrane in a manner allowing subsequent detection of nucleic acid on or recovery of nucleic acid from a region of said membrane which is spaced from the sample receiving section.

* * * * *